US008569332B2

(12) United States Patent
Wasik et al.

(10) Patent No.: US 8,569,332 B2
(45) Date of Patent: Oct. 29, 2013

(54) O-METHYLATED RAPAMYCIN DERIVATIVES FOR ALLEVIATION AND INHIBITION OF LYMPHOPROLIFERATIVE DISORDERS

(75) Inventors: Mariusz A. Wasik, Ardmore, PA (US); Leslie M. Shaw, Audubon, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 12/795,335

(22) Filed: Jun. 7, 2010

(65) Prior Publication Data
US 2010/0290994 A1 Nov. 18, 2010

Related U.S. Application Data

(60) Division of application No. 10/192,193, filed on Jul. 9, 2002, now Pat. No. 7,754,734, which is a continuation of application No. PCT/US01/01537, filed on Jan. 12, 2001.

(60) Provisional application No. 60/176,086, filed on Jan. 14, 2000.

(51) Int. Cl.
*A61K 31/535* (2006.01)

(52) U.S. Cl.
USPC .......................................... 514/291

(58) Field of Classification Search
USPC .......................................... 514/291
See application file for complete search history.

(56) References Cited

U.S. PATENT DOCUMENTS

| | | | |
|---|---|---|---|
| 4,401,653 A | 8/1983 | Eng | |
| 4,699,783 A | 10/1987 | Terman et al. | |
| 5,206,018 A | 4/1993 | Sehgal et al. | |
| 5,258,389 A | 11/1993 | Goulet et al. | |
| 5,525,610 A | 6/1996 | Caufield et al. | |
| 5,527,907 A | 6/1996 | Or et al. | |
| 5,665,772 A | 9/1997 | Cottens et al. | |
| 6,362,164 B1 | 3/2002 | Weckbecker | |
| 6,399,625 B1 | 6/2002 | Zhu | |
| 6,399,626 B1 | 6/2002 | Zhu et al. | |
| 6,432,973 B1 | 8/2002 | Zhu et al. | |
| 6,440,990 B1 | 8/2002 | Cottens et al. | |
| 6,440,991 B1 | 8/2002 | Zhu et al. | |

FOREIGN PATENT DOCUMENTS

| | | | |
|---|---|---|---|
| EP | 0 525 960 A1 | 2/1993 | |
| EP | 9409010 | * 4/1994 | |
| WO | WO 94/09010 A1 | 4/1994 | |
| WO | WO 00/67773 | 11/2000 | |

OTHER PUBLICATIONS

Beatty et al., "Effect of cyclosporine and tacrolimus on the growth of Epstein-Barr virus-transformed B-cell lines." Transplantation 65: 1248-1255 (1998).
Beers et al., in "The Merck Manual of Diagnosis and Therapy," 17th ed, chapters 138-139, pp. 944-962 (1999).
Bohler et al., "The In Vivo Effect of Rapamycin Derivative SDZ RAD on Lymphocyte Proliferation," Transplantation Proceedings,30: 2195-2197 (1998).
Cesarman et al., "In vitro establishment and characterization of two acquired immunodeficiency syndrome-related lymphoma cell lines (BC-1 and BC-2) containing Kaposi's sarcoma-associated herpesvirus-like (KSHV) DNA sequences," Blood 86: 2708-2714 (1995).
Curtis et al., "Risk of lymphoproliferative disorders after bone marrow transplantation: a multi-institutional study," Blood 94: 2208-2216 (1999).
Devergne et al., "Role of the TRAF binding site and NF-kappaB activation in Epstein-Barr virus latent membrane protein 1-induced cell gene expression." J. Virol. 72: 7900-7908 (1998).
Douglas et al., "Novel approach for simultaneous evaluation of cell phenotype, apoptosis, and cell cycle using multiparameter flow cytometry," Cytometry 32: 57-65 (1998).
Eliopoulos et al., "CD40-induced growth inhibition in epithelial cells is mimicked by Epstein-Ban Virus-encoded LMP1: involvement of TRAF3 as a common mediator," Oncogene 13: 2243-2254 (1996).
Flanagan et al., "Rapamycin inhibits p34cdc2 expression and arrests T lymphocyte proliferation at the Gl/S transition," Ann N.Y. Acad. Sci. 696: 31-37 (1993).
Gottschalk et al., "Identification of immunosuppressant-induced apoptosis in a murine B-cell line and its prevention by bcl-x but not bcl-2," Proc. Natl. Acad. Sci. USA 91: 7350-7354 (1994).
Halkos et al., "Thoracic Presentation of Posttransplant Lymphoproliferative Disorders," Chest 126:2013-2020 (2004).
Harris et al., "Posttransplant lymphoproliferative disorders: summary of Society for Hematopathology Workshop," Semin. Diagn. Path 14: 8-14 (1997).
Harris et al., "Post-transplant Lymphoproliferative Disorders," in Pathology and Genetics, Jaffe et al eds, IARC Press, pp. 264-267 (2002).
Hausen et al., "Suppression of acute rejection in allogeneic rat lung transplantation: a study of the efficacy and pharmacokinetics of rapamycin derivative (SDZ RAD) used alone and in combination with a microemulsion formulation of cyclosporine," J. Heart Lung Transplant 18: 150-159 (1999).
Hosoi et al., "Rapamycin causes poorly reversible inhibition of mTOR and induces p53-independent apoptosis in human rhabdomyosarcoma cells," Cancer Res. 59: 886-894 (1999).
Kawamata et al., "The upregulation of p27Kipl by rapamycin results in G1 arrest in exponentially growing T-cell lines," Blood 91: 561-569 (1998).
Liebowitz, "Epstein-Ban virus and a cellular signaling pathway in lymphomas from immunosuppressed patients," New Eng. J. Med. 338: 1413-1421 (1998).

(Continued)

*Primary Examiner* — Melenie McCormick
*Assistant Examiner* — Timothy E Betton
(74) *Attorney, Agent, or Firm* — Riverside Law LLP

(57) ABSTRACT

The present invention relates to methods of alleviating and inhibiting a lymphoproliferative disorder in a mammal, the method comprising administering one or more rapamycin derivatives (including rapamycin) to the mammal. Further, the invention provides a method for identifying agents which are useful for alleviating and inhibiting a lymphoproliferative disorders, as well as a method for identifying agents which are capable of inhibiting metastasis of lymphatic tumors in a mammal.

2 Claims, 8 Drawing Sheets

(56) References Cited

OTHER PUBLICATIONS

Maeda et al., "Origin of human T-lymphotrophic virus I-positive T cell lines in adult T cell leukemia. Analysis of T cell receptor gene rearrangement," Exp. Med. 162: 2169-2174 (1985).

Miki et al., "Tacrolimus enhances the immunosuppressive effect of cyclophosphamide but not that of leflunomide or mycophenolate mofetil in a model of discordant liver xenotransplantation," Transplant Proc. 30: 1091-1092 (1998).

Morrison et al., "Clinical characteristics of post-transplant lymphoproliferative disorders," Am. J. Med. 97: 14-24 (1994).

Mosialos et al., "The Epstein-Barr virus transforming protein LMP1 engages signaling proteins for the tumor necrosis factor receptor family," Cell 80: 389-399 (1995).

Muthukkumar et al., "Rapamycin, a potent immunosuppressive drug, causes programmed cell death in B lymphoma cells," Transplanation 60: 264-270 (1995).

Pasqualucci et al., "Antitumor activity of anti-CD30 immunotoxin (Ber-H2/saporin) in vitro and in severe combined immunodeficiency disease mice xenografted with human CD30+ anaplastic large-cell lymphoma," Blood 85: 2139-2146 (1995).

Pepper et al., "Flow cytometric assessment of three different methods for the measurement of in vitro apoptosis," Leuk. Res. 22: 439-444 (1998).

Poiesz et al., "Detection and isolation of type C retrovirus particles from fresh and cultured lymphocytes of a patient with cutaneous T-cell lymphoma," Proc. Natl. Acad. Sci. USA 77: 7415-7419 (1980).

Popovic et al., "Isolation and transmission of human retrovirus (human t-cell leukemia virus)," Science 219: 856-859 (1983).

Pullen et al., "CD40—tumor necrosis factor receptor—associated factor (TRAF) interactions: regulation of CD40 signaling through multiple TRAF binding sites and TRAF hetero-oligomerization," Biochemistry 37: 11836-11845 (1998).

Rochford et al., "Common and idiosyncratic patterns of cytokine gene expression by Epstein-Barr virus transformed human B cell lines," Viral Immunol. 10: 183-195 (1997).

Sakata et al., "Involvement of a rapamycin—sensitive pathway in CD40—mediated activation of murine B cells in vitro," Immunology Letters 68: 301-309 (1999).

Schuler et al., "SDZ RAD, a new rapamycin derivative: pharmacological properties in vitro and in vivo," Transplantation 64: 36-42 (1997).

Schuurman et al., "SDZ RAD, a new rapamycin derivative: synergism with cyclosporine," Transplantation 64: 32-35 (1997).

Schuurman et al., "The macrolide SDZ RAD is efficacious in a nonhuman primate model of allotransplantation," Transplant Proc. 30: 2198-2199 (1998).

Sehgal, "Rapamune® (RAPA, rapamycin, sirolimus): mechanism of action immunosuppressive effect results from blockade of signal transduction and inhibition of cell cycle progression," Clin. Biochem. 31: 335-340 (1998).

Sedrani et al., "Chemical Modifiation of Rapamycin: The Discovery of SDZ RAD," Transplantation Proceedings 30: 2192-2194 (1998).

Shi et al., "Rapamycin enhances apoptosis and increases sensitivity to cisplatin in vitro," Cancer Res. 55: 1982-1988 (1995).

Sigal et al., "Cyclosporin A, FK-506, and rapamycin: pharmacologic probes of lymphocyte signal transduction," Ann. Rev. Immunol. 10: 519-560 (1992).

Silberstein et al., "Variable region gene analysis of pathologic human autoantibodies to the related i and I red blood cell antigens," Blood 78: 2372-2386 (1991).

Terada et al., "Rapamycin blocks cell cycle progression of activated T cells prior to events characteristic of the middle to late G1 phase of the cycle," J. Cell Physiol. 154: 7-15 (1993).

Visonneau et al., "Growth characteristics and metastatic properties of human breast cancer xenografts in immunodeficient mice," Am. J. Path. 152: 1299-1311 (1998).

Warnke et al., in "Tumors of the Lymph Nodes and Spleen," in Atlas of Tumor Pathology, AFIP Third Series, Fascicle 14: 531-535 (1995).

Wasik et al., "Constitutive secretion of soluble interleukin-2 receptor by human T cell lymphoma xenografted into SCID mice. Correlation of tumor volume with concentration of tumor-derived soluble interleukin-2 receptor in body fluids of the host mice," Am. J. Path 144: 1089-1097 (1994).

Zhang et al., "Activation of Jak/STAT proteins involved in signal transduction pathway mediated by receptor for interleukin 2 in malignant T lymphocytes derived from cutaneous anaplastic large T-cell lymphoma and Sezary syndrome," Proc. Natl. Acad. Sci. USA 93: 9148-9153 (1996).

Zhang et al., "Differences in phosphorylation of the IL-2R associated JAK/STAT proteins between HTLV-I(+), IL-2-independent and IL-2-dependent cell lines and uncultured leukemic cells from patients with adult T-cell lymphoma/leukemia," Leukemia Res. 23: 373-384 (1999).

Herrera et al., "Treatment of SCID/Human B Cell Precursor ALL with Anti-CD19 and Anti-CD22 Immunotoxins," Leukemia 17:334-338 (2003).

Majewski et al., "Immunosuppressive TOR Kinase Inhibitor Everolimus (RAD) Suppresses Growth of Cells Derived from Post-transplant Lymphoproliferative Disorder at Allograft-Protecting Doses," Transplantation 75:1710-1717 (2003).

Schmidt-Wolf et al., "Use of a SCID Mouse/Human Lymphoma Model to Evaluate Cytokine-Induced Killer Cells with Potent Antitumor Cell Activity," J. Exp. Med. 174:139-149 (1991).

Winkler, "Cyclosporin as Baseline Immunosuppression in Solid Organ Transplantation," BioDrugs 14:185-193 (2000).

Simone, J.V., Part XIV Oncology—154 Introduction. In J.C. Bennett and F. Plum eds. *Cecil Textbook of Medicine*. 20th ed., 1996, vol. 1, pp. 1004-1008.

\* cited by examiner

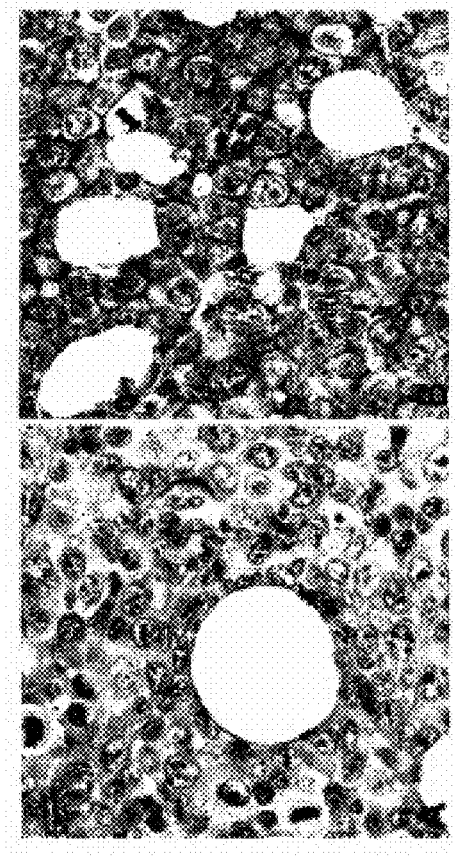

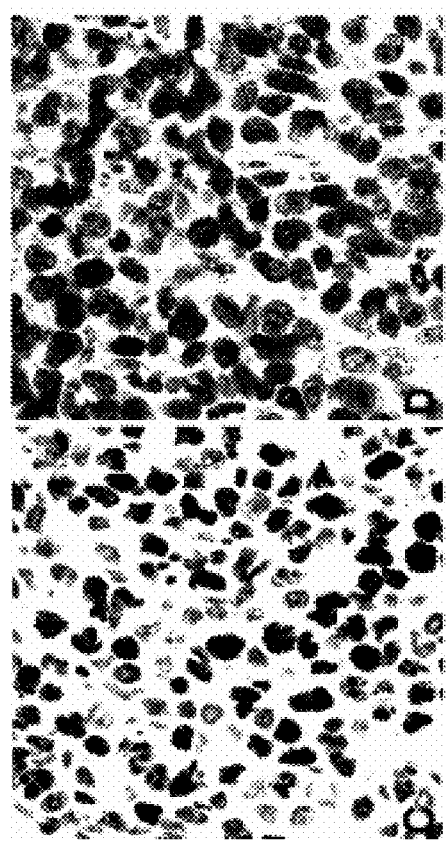

O-METHYLATED RAPAMYCIN DERIVATIVES FOR ALLEVIATION AND INHIBITION OF LYMPHOPROLIFERATIVE DISORDERS

CROSS REFERENCE TO RELATED APPLICATIONS

This application is a divisional of U.S. application Ser. No. 10/192,193, filed Jul. 9, 2002, now U.S. Pat. No. 7,754,734 now allowed, which is a continuation of PCT/US01/01537, filed Jan. 12, 2001, which claims the benefit pursuant to 35 U.S.C. §119(e) of U.S. provisional patent application 60/176,086, which was filed on Jan. 14, 2000, which are each incorporated herein in their entirety by reference.

BACKGROUND OF THE INVENTION

Post-transplant lymphoproliferative disorders (PTLDs) which usually involve expansion of B lymphocytes infected with the Epstein-Barr virus (EBV), are a life-threatening complication of the immunosupressive therapy necessary to inhibit graft rejection (Morrison et al., 1994, Am. J. Med. 97:14-24; Warnke et al., 1995, AFIP Fascicle 14:531-535). PTLDs comprise a whole spectrum of lymphoproliferative disorders ranging from a polyclonal atypical lymphoid hyperplasia to a monoclonal, overtly malignant B-cell lymphoma (Morrison et al., 1994, Am. J. Med. 97:14-24; Warnke et al., 1995, AFIP Fascicle 14:531-535; Curtis et al., 1999, Blood 94:2208-2216; Harris et al., 1997, Semin. Diagn. Path. 14:8-14). Less advanced forms of PTLDs respond to a less aggressive course of immunosuppressive therapy (Morrison et al., 1994, Am. J. Med. 97:14-24; Sigal et al., 1992, Ann. Rev. Immunol. 10:519-60). However, lowering the dose of standard immunosuppressive drugs, which nullify the body's ability to reject and destroy foreign tissue, can jeopardize the survival of a graft. Moreover, this modification in treatment with conventional agents is not effective against malignant, lymphoma-type PTLDs which are usually fatal for the graft recipient.

Lymphoma causes significant morbidity and mortality, accounting for more than 50,000 new diagnoses annually in the United States alone. Many lymphomas are either Hodgkin's or non-Hodgkin's lymphomas, which can be derived from peripheral, mature B, T, or NK lymphomas. Based on their natural course, non-Hodgkin's lymphomas are classified into low, intermediate, and high grades. Low grade lymphomas are usually slowly progressive, but are essentially non-curable. The current 5-year disease-free, post-therapy survival rate for the intermediate and high grade lymphomas is approximately 60%. These aggressive types of lymphoma result in a rapid demise of the patients who do not respond to therapy. Prognosis of lymphomas occurring in patients who are immunocompromised such as AIDS and post-transplant patients, is particularly poor. Therefore, new treatment modalities are needed to improve cure rate of lymphoma.

SDZ RAD (40-O-{2-hydroxyethyl}-rapamycin) is one of a class of rapamycin derivatives which exhibit immunosuppressive activities (PCT application WO 94/09010; Schuurman et al., 1997, Transplantation 64:32-5; Schuler et al. 1997, Transplantation 64:36-42; Sedrani, et al., 1998, Transplant. Proc. 30:2192-2194; Schuurman et al., 1998, Transplant Proc. 30:2198-2199; Hausen et al., 1999, J. Heart Lung Transplant 18:150-159). Compounds of this class, including rapamycin, have several points of action in normal T lymphocytes. They inhibit primarily down-stream signaling events mediated by the IL-2 receptor (Seghal, 1998, Clin. Biochem. 31:335-340) and other cytokine receptors (Sakata et al., 1999, Immunology Letters 68:301-309), but also affect cell-cycle progression at the early $G_1$ phase (Terada et al., 1993, J. Cell Physiol. 154:7-15; Flanagan et al., 1993, Ann. N.Y. Acad. Sci. 696:31-37). The multi-faceted immunosuppressive activities exhibited by SDZ RAD and other O-alkylated rapamycin derivatives compounds make these compounds versatile immunosuppressive agents.

There is a significant need for more effective therapeutic and prophylactic methods for limiting the severity and frequency of lymphoproliferative disorders such as lymphomas and PTLDs. The present invention satisfies this need.

BRIEF SUMMARY OF THE INVENTION

The invention includes a method of alleviating a lymphoproliferative disorder in a human patient. The method comprises administering to the patient, in an amount sufficient to alleviating the disorder, a rapamycin derivative having the chemical structure shown in Formula I in FIG. 8. In a preferred embodiment, the rapamycin derivative is 40-O-(2-hydroxy)ethyl-rapamycin. Numerous other useful rapamycin derivatives (including rapamycin itself) are described in this disclosure. Lymphoproliferative disorders that can be alleviated using this method include, for example, PTLDs and lymphatic cancers such as lymphomas. The method can also be used to alleviate lymphoproliferative disorders caused or associated with treatment of the patient by immunosuppressive therapy (e.g., immunosuppressive therapy associated with tissue transplantation).

In another method included in the invention, a lymphoproliferative disorder is inhibited or prevented in a patient at risk for developing such a disorder (e.g., an immunocompromised patient or a patient undergoing immunosuppressive therapy).

In these methods, the rapamycin derivative can be co-administered (in a single composition or in discretely-administered compositions) with a second pharmacologically active agent, such as an immunosuppressive agent. Immunosuppressive agents are known for use in methods of inhibiting graft rejection, and those known methods can be improved by administering both the immunosuppressive agent and a rapamycin derivative disclosed herein to a patient who has received a graft.

The invention also includes a method of inhibiting metastasis of a lymphatic tumor in a human patient afflicted with a lymphatic cancer. This method comprising administering to the patient, in an amount sufficient to inhibit lymphocyte proliferation, a rapamycin derivative having the chemical structure shown in Formula I.

In another aspect, the invention includes a method of assessing whether an agent is useful for alleviating or inhibiting a lymphoproliferative disorder in a human patient. This method comprising transforming a B lymphocyte with an Epstein-Barr virus, injecting the lymphocyte into a mouse having a severe combined immunodeficiency, administering the agent to the mouse, and monitoring tumor growth in the mouse for at least about 21 days. If one or more of tumor regression, tumor eradication, and absence of a second tumor is observed in the mouse, then this is an indication that the agent is useful for alleviating or inhibiting a post-transplant lymphoproliferative disorder in a mammal.

BRIEF DESCRIPTION OF THE DRAWINGS

FIG. 4, comprising FIGS. 4A-4D, is a group of images of photomicrographs which depict the morphology and phenotype of 20A tumors xenotransplanted into SCID mouse. In FIG. 4A, hematoxylin-eosin stain shows large cell lymphoma with high mitotic rate. In FIG. 4B, immunoperoxidase stain using an antibody which binds specifically with human CD20 (i.e., a B-cell antigen) shows cell-membrane staining in all lymphoma cells. In FIG. 4C, immunoperoxidase stain using an antibody which binds specifically with Ki67 (i.e., a cell proliferation-related antigen) shows nuclear staining in 50-80% of cells. In FIG. 4D, in-situ hybridization for EBV-encoded EBER-1 RNA shows nuclear positivity in all lymphoma cells.

FIG. 5, comprising

FIG. 6, comprising

DETAILED DESCRIPTION OF THE INVENTION

The present invention relates to methods of alleviating or inhibiting lymphoproliferative disorders such as lymphomas and post-transplant lymphoproliferative disorders (PTLDs) in a mammal such as a human. The method comprises administering to the mammal an O-alkylated rapamycin derivative such as SDZ RAD in amount sufficient to inhibit proliferation of lymphocytes in the mammal.

O-alkylated rapamycin derivatives are known to inhibit graft rejection. Thus, when the rapamycin derivative is administered to a mammal which has undergone a tissue or organ graft (i.e., a xenograft), administration of one of these derivatives can both inhibit graft rejection and alleviate or prevent a PTLD. For treatment or inhibition of a PTLD, the amount administered can be sufficient to inhibit both graft rejection and proliferation of lymphocytes.

Not previously recognized by others is the fact that O-alkylated rapamycin derivatives such as those described herein can be used to alleviate or prevent lymphoma. O-alkylated rapamycin derivative such as SDZ RAD can also be used to inhibit proliferation of lymphocytes, as occurs in a variety of lymphoproliferative disorders other than lymphoma (e.g., chronic lymphocytic leukemia). O-alkylated rapamycin derivatives such as SDZ RAD can be used to induce in a cell, either in vitro or in vivo, cell cycle arrest or apoptosis, and to inhibit lymphocyte growth and proliferation.

The O-alkylated rapamycin derivatives that are useful in the methods described herein have been described by others, as has methods for making them. In this regard, the PCT patent application having international publication number WO 94/09010 is incorporated herein by reference.

Figure 8:
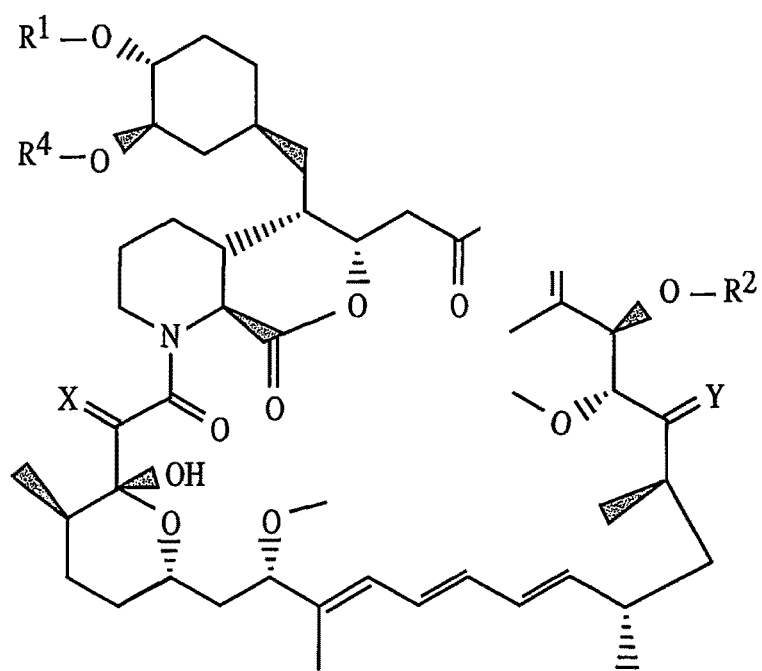
FIG. 8 depicts the chemical formula for O-methylated rapamycin derivatives which can be used in the methods described herein (i.e., Formula I).

O-alkylated rapamycin derivatives that are useful in the methods described in this disclosure include those having the chemical structure shown in Formula I in FIG. 8, wherein X is (H, H) or O;

Y is (H, OH) or O;

each of $R^1$ and $R^2$ is independently selected from the group consisting of —H, alkyl, thioalkyl, arylalkyl, hydroxyalkyl, dihydroxyalkyl, hydroxyalkylarylalkyl, dihydroxyalkylarylalkyl, alkoxyalkyl, acyloxyalkyl, aminoalkyl, alkylaminoalkyl, alkoxycarbonylaminoalkyl, acylaminoalkyl, arylsulfonamidoalkyl, allyl, dihydroxyalkylallyl, dioxolanylallyl, carbalkoxyalkyl, and $(R^3)_3$ Si;

each $R^3$ is independently selected from the group consisting of —H, methyl, ethyl, isopropyl, tert-butyl, and phenyl; and either $R^4$ is methyl or $R^4$ and $R^1$ together form a $C_{2-5}$ alkylene moiety.

In the descriptions of $R^1$-$R^4$, "alk-" or "alkyl" refers to a $C_{1-6}$ alkyl moiety, the moiety being branched or linear, and preferably being a $C_{1-3}$ alkyl moiety, in which the carbon chain can, optionally, be interrupted by an ether (—O—) linkage (e.g., —CH$_2$—CH$_2$—O—CH$_2$—). In the descriptions of $R^1$-$R^4$, "ar-" or "aryl" refers to a $C_{5-8}$ aryl moiety, the aryl moiety optionally having one or two nitrogen atoms in place of a carbon atom. In the descriptions of $R^1$-$R^4$, "allyl" means —CH$_2$—CH═CH$_2$. In the descriptions of $R^1$-$R^4$, "acyl" refers to a $C_{1-6}$ alkanoyl moiety (i.e., an alkyl moiety having a carbonyl {i.e., —CO—} moiety in place of a methylene moiety {i.e., —CH$_2$—} moiety of the alkyl moiety). In the descriptions of $R^1$-$R^4$, "alkylene" refers to a $C_{1-6}$ alkylene moiety, the moiety being branched or linear.

Examples of O-alkylated rapamycin derivatives that are suitable for use in the methods described in this disclosure include 40-O-benzyl-rapamycin,
40-O-(4'-hydroxymethyl)benzyl-rapamycin,
40-O-[4'-(1,2 dihydroxyethyl)]benzyl-rapamycin,
40-O-Allyl-rapamycin,
40-O-[3'-(2,2-dimethyl-1,3-dioxolan-4(S)-yl)-prop-2'-en-1'-yl]-rapamycin,
(2'E,4'S)-40-O-(4',5'-dihydroxypent-2'-en-1'-yl)-rapamycin,
40-O-(2-hydroxy)ethoxycarbonylmethyl-rapamycin,
40-O-(2-hydroxy)ethyl-rapamycin,
40-O-(3-hydroxy)propyl-rapamycin,
40-O-(6-hydroxy)hexyl-rapamycin,
40-O-[2-(2hydroxy)ethoxy]ethyl-rapamycin,
40-O-[(3S)-2,2-dimethyldioxolan-3-yl]methyl-rapamycin,
40-O-[(2S)-2,3-dihydroxyprop-1-yl]-rapamycin, 40-O-(2-acetoxy)ethyl-rapamycin,
40-O-(2-nicotinoyloxy)ethyl-rapamycin,
40-O-[2-(N-morpholino)acetoxy]ethyl-rapamycin,
40-O-(2-N-imidazolylacetoxy)ethyl-rapamycin,
40-O-[2-(N-methyl-N'-piperazinyl)acetoxy]ethyl-rapamycin,
39-O-desmethyl-39,40-O,O-ethylene-rapamycin,
(26R)-26-dihydro-40-O-(2-hydroxy)ethyl-rapamycin,
28-O-methyl-rapamycin,
40-O-(2-aminoethyl)-rapamycin,
40-O-(2-acetaminoethyl)-rapamycin,
40-O-(2-nicotinamidoethyl)-rapamycin,
40-O-(2-(N-methyl-imidazo-2'-ylcarbethoxamido)ethyl)-rapamycin,
40-O-(2-ethoxycarbonylaminoethyl)-rapamycin,
40-O-(2-tolylsulfonamidoethyl)-rapamycin, and
40-O-[2-(4'5'-dicarboethoxy-1',2',3'-triazol-1'-yl)-ethyl]-rapamycin.

Figure 7:
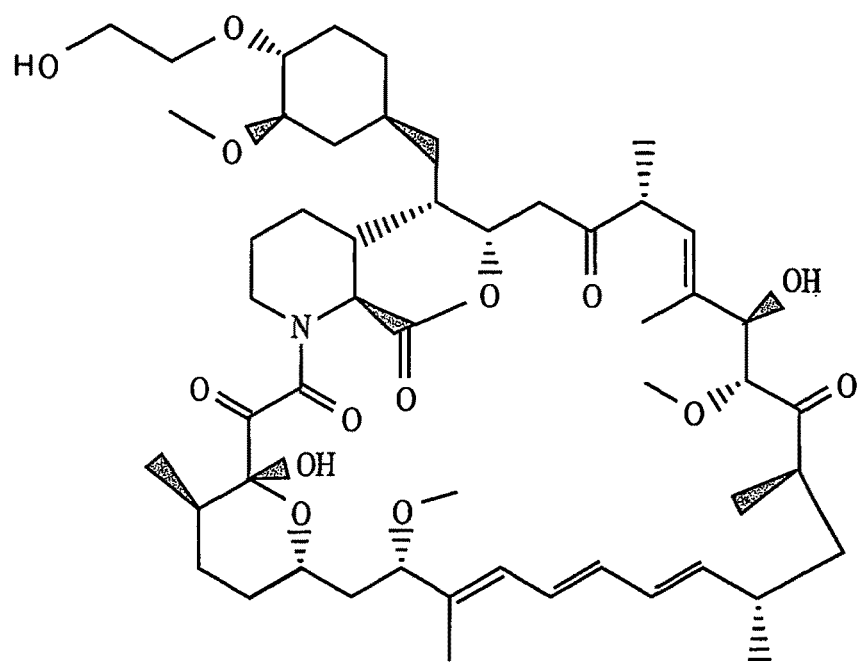
FIG. 7 depicts the chemical structure of SDZ RAD.

Preferred compounds for use in the methods described herein are 40-O-substituted rapamycins where X and Y are both O, $R^2$ is H, $R^4$ is methyl, and $R^1$ is selected from hydroxyalkyl, hydroxyalkoxyalkyl, acylaminoalkyl, and aminoalkyl. Examples of preferred compounds include 40-O-(2-hydroxy)ethyl-rapamycin (i.e., SDZ RAD, the structure of which is shown in FIG. 7), 40-O-(3-hydroxy) propyl-rapamycin, 40-O-[2-(2-hydroxy)ethoxy]ethyl-rapamycin, and 40-O-(2-acetaminoethyl)-rapamycin. Rapamycin itself (i.e., the compound having the structure of Formula I, wherein $R^1$ and $R^2$ are each —H, $R^4$ is methyl, and each of X and Y are O) can also be used in the methods described herein.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

A process in a cell, such as cell growth, cell cycle progression, proliferation, or tumorigenesis, is "inhibited" by a composition or method of treatment if, upon administering the composition to the cell or employing the method of treatment on the cell, the process is altered relative to the same process in a cell to which the composition was not administered or on which the method of treatment was not employed. For example, if the level of proliferation in a cell is decreased following administration of a composition comprising SDZ RAD, as compared with the level of proliferation in a cell to which the composition is not administered, then the composition inhibits proliferation in the cell.

A process in a mammal, such as tumor growth, establishment of a tumor, a lymphoproliferative response, or graft rejection, is "inhibited" by a composition or method of treatment if, upon administering the composition to the mammal or employing the method of treatment on the mammal, the process is decreased in rate or magnitude relative to the same process in a mammal to which the composition was not administered or on which the method of treatment was not employed. For example, if the level of proliferation of lymphocytes in a mammal is decreased following administration of a composition comprising SDZ RAD, as compared with the level of proliferation of lymphocytes in a mammal to which the composition is not administered, then the composition inhibits a proliferation of lymphocytes in the mammal.

A process in a cell, such as apoptosis or cell cycle arrest, is "induced" by a composition or method of treatment if, upon administering the composition to the cell or employing the method of treatment on the cell, the level of the process in the cell is increased relative to the process in a cell to which the composition was not administered or on which the method of treatment was not employed. For example, if the degree, level, or likelihood of apoptosis in a cell is increased following administration of a composition comprising SDZ RAD, as compared with the degree, level, or likelihood of apoptosis in a cell to which the composition is not administered, then the composition induces apoptosis in the cell.

As used herein, the term "pharmaceutically acceptable carrier" means a chemical composition with which an O-alkylated rapamycin derivative can be combined and which, following the combination, can be used to administer the rapamycin derivative to a subject.

As used herein, the term "physiologically acceptable" ester or salt means an ester or salt form of an O-alkylated rapamycin derivative which is compatible with any other ingredients of the pharmaceutical composition and which is not deleterious to the subject to which the composition is to be administered.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration can include, but is not limited to, subcutaneous, intraperitoneal, intramuscular, intrasternal injection, and kidney dialytic infusion techniques.

A first pharmacological agent and a second pharmacological agent are "co-administered" if the two agents are administered sufficiently closely in time that the period during which the pharmacological effect attributable to the first agent is at least half its maximal value overlaps with the period during which the pharmacological effect attributable to the second agent is at least half its maximal value. Co-administered agents can be administered in a single composition containing the agents, or they can be administered in discrete compositions.

As used herein, the term "induction of apoptosis" means a process which causes a cell to begin or accelerate the process of programmed cell death.

A disorder is "alleviated" if the severity of the disorder or one of its symptoms or the frequency with which the disorder or one of its symptoms is experienced by a patient is reduced.

A disorder is "inhibited" by a treatment if the onset of the disorder or one of its symptoms is delayed or prevented, relative to its onset in the absence of the treatment.

Description

The present invention relates to a method of using an O-alkylated rapamycin derivative to alleviate or inhibit a lymphoproliferative disorder in a mammal. Lymphoproliferative disorders which can be alleviated or inhibited using the method described herein include post-transplant lymphoproliferative disorders (PTLDs), lymphomas, and other disorders. This method comprises administering to the mammal a sufficient amount of an O-alkylated rapamycin derivative to inhibit the disorder. In patients who are afflicted with both a lymphoproliferative disorder and graft rejection, an amount of the derivative sufficient to alleviate or inhibit both the disorder and the graft rejection can be administered. For example, both rejection of a graft (i.e., a transplanted tissue or organ) and a PTLD can be alleviated simultaneously.

PTLDs include a wide spectrum of lymphoproliferative disorders, ranging from a polyclonal atypical lymphoid hyperplasia to a monoclonal, overtly malignant B cell lymphoma. Examples of such disorders have been described in the art (e.g., Morrison et al., 1994, Am. J. Med. 97:14-24; Warnke et al., 1995, AFIP Fascicle 14:531-535; Curtis et al., 1999, Blood 94:2208-2216; Harris et al., 1997, Semin. Diagn. Path. 14:8-14) and can be identified by the skilled artisan.

One class of lymphoproliferative disorders for which the methods described herein are useful are those disorders which are characterized by infection of lymphocytes by Epstein-Barr virus (EBV). Proliferation of EBV-infected lymphocytes is a frequent complication of immunosuppressive therapy, and thus sometimes occurs during immunosuppression associated with prevention of graft rejection, with cancer-related chemotherapy, or with other immune-suppressing medical interventions. Furthermore, proliferation of EBV-infected lymphocytes can be accelerated in immuno-compromised patients, such as patients afflicted with AIDS or other immune disorders. The O-alkylated rapamycin derivatives described herein can be used before, after, or during treatment of one of these other immune system-affecting disorders or treatments. For example, a patient who is to undergo immunosuppressive therapy can first (i.e., minutes, hours, days, or weeks beforehand) be administered one or more O-alkylated rapamycin derivatives (including rapamycin) in order to inhibit or prevent proliferation of lymphocytes during the immunosuppressive therapy. One or more O-alkylated rapamycin derivatives (including rapamycin) can be co-administered (i.e., in a single composition or in discrete compositions administered closely in time or alternately) during the course of immunosuppressive therapy in order to decrease or prevent proliferation of lymphocytes during the therapy. The derivative(s) need not be the same one(s), if any, administered prior to the therapy. Similarly, one or more O-alkylated rapamycin derivatives (including rapamycin) can also (or instead) be administered to a patient who has undergone immunosuppressive therapy, in order to alleviate, inhibit, or prevent post-therapy lymphocyte proliferation and symptoms associated therewith.

A particular method included within the scope of the invention comprises administering SDZ RAD to a human prior to transplantation of a tissue (i.e., an allograft or a xenograft) into or onto the body of the human. Such administration can occur before, during, or after transplantation, or at any combination of these. By way of example, SDZ RAD can be administered to a human patient prior to, during, and after receiving an allogeneic kidney transplant. Other examples of transplants include allogeneic heart, kidney, and liver transplants, heart valves, vascular grafts, skin grafts, dura mater grafts, pericardium grafts, cartilage grafts and implants, and xenogeneic transplants.

Another type of lymphoproliferative disorder that can be, but often is not, associated with tissue transplantation is lymphatic cancers, including lymphomas and lymphocytic leukemias. The lymphocytic leukemias include disorders such as acute and chronic lymphocytic leukemias. Lymphomas encompass a wide variety of cancers characterized by lymphocyte proliferation. Examples of lymphomas include AIDS-related lymphomas, Hodgkin's lymphoma (sometimes designated Hodgkin's disease), non-Hodgkin's lymphoma, Burkitt's lymphoma, diffuse large cell lymphoma, T-cell lymphoma, and cutaneous T-cell lymphoma.

Regardless of whether a patient is diagnosed with a disease or exhibits symptoms of a disease, it can be desirable to inhibit lymphocyte proliferation to a patient who harbors lymphocytes infected with EBV, particularly if the patient is expected to undergo immunosuppressive therapy or if the patient is at particular risk for developing an immune-compromising disorder. Such patients can be identified by isolating lymphocytes from the patient and assessing the presence or absence of all or part of the EBV genome in those lymphocytes. If EBV is detected, administration of rapamycin or an O-alkylated rapamycin derivative can be indicated.

The methods described herein for inhibiting or alleviating a lymphoproliferative disorder comprise administering rapamycin or an O-alkylated rapamycin derivative to a mammal. The precise form in which the compound is administered is not critical, numerous pharmaceutical compositions, dosage forms, and pharmaceutically acceptable carriers and excipients being known in the art. A formulation administered to a mammal can contain the rapamycin derivative as the sole active agent, or it can be admixed with one or more other active agents (e.g., an immunosuppressive agent such as azathioprine, a mycophenolic acid such as mycophenolate mofetil, $Rh_o(D)$ immune globulin, cyclosporin, tacrolimus, cisplatin, a cyclophosphamide, and leflunomide).

The invention encompasses the preparation and use of medicaments and pharmaceutical compositions comprising one or more O-alkylated rapamycin derivatives (including rapamycin) as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. Administration of one of these pharmaceutical compositions to a subject is useful for inhibiting proliferation of lymphocytes in the subject, as described elsewhere in the present disclosure. The active ingredient may be present in the pharmaceutical composition in the form of a physiologically acceptable ester or salt, such as in combination with a physiologically acceptable cation or anion, as is well known in the art.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to other mammals. Modification of pharmaceutical compositions suitable for administration to humans in order to render the compositions suitable for administration to animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, and mammals including commercially relevant mammals such as cattle, pigs, horses, sheep, cats, and dogs.

Pharmaceutical compositions that are useful in the methods of the invention may be prepared, packaged, or sold in formulations suitable for oral, rectal, vaginal, parenteral, topical, pulmonary, intranasal, buccal, ophthalmic, or another route of administration, although parental administration is contemplated to be the most readily effective method of administering rapamycin derivatives for the purpose of alleviating, inhibiting, or preventing lymphoproliferative disorders.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient. A unit dose of a pharmaceutical composition of the invention will generally comprise from about 50 micrograms to about 50 milligrams of the active ingredient, and preferably comprises from about 500 micrograms to about 10 milligrams of the active ingredient. In general, O-alkylated rapamycin derivatives can be used in amounts on the same order of magnitude as presently-used amounts of rapamycin (e.g., 1-5 milligrams per unit dose).

In addition to the active ingredient, a pharmaceutical composition of the invention may further comprise one or more additional pharmaceutically active agents. Particularly contemplated additional agents include immunosuppressive agents such as azathioprine, a mycophenolic acid such as mycophenolate mofetil, $Rh_o(D)$ immune globulin, cyclosporin, tacrolimus, cisplatin, a cyclophosphamide, and leflunomide.

Controlled- or sustained-release formulations of a pharmaceutical composition of the invention may be made using conventional technology.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules, in multi-dose containers containing a preservative, or in single-use devices for auto-injection or injection by a medical practitioner. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

A pharmaceutical composition of the invention may be administered to deliver a dose of between 10 micrograms per kilogram body weight per day and 1.5 milligrams per kilogram body weight per day and, and preferably to deliver of between 20 and 700 micrograms per kilogram body weight per day, to a subject. For adult humans, administration of 0.1 to 50 milligrams per day of rapamycin or an O-alkylated rapamycin derivative, and preferably 1 to 10 milligrams per day of the active ingredient is contemplated.

It is understood that the ordinarily skilled physician or veterinarian will readily determine and prescribe an effective amount of the compound to alleviate or inhibit a lymphoproliferative disorder in the subject. In so proceeding, the physician or veterinarian may, for example, prescribe a relatively low dose at first, subsequently increasing the dose until an appropriate response is obtained. It is further understood, however, that the specific dose level for any particular subject will depend upon a variety of factors including the activity of the specific compound employed, the age, body weight, general health, gender, and diet of the subject, the time of administration, the route of administration, the rate of excretion, any drug combination, and the severity of the lymphoproliferative disorder being treated or inhibited.

Another aspect of the invention relates to a kit comprising a pharmaceutical composition of the invention and an instructional material. As used herein, an "instructional material" includes a publication, a recording, a diagram, or any other medium of expression which is used to communicate the usefulness of the pharmaceutical composition of the invention for inhibiting proliferation of lymphocytes or alleviating or inhibiting a lymphoproliferative disorder. The instructional material can also, for example, describe an appropriate dose of the pharmaceutical composition of the invention. The instructional material of the kit of the invention may, for example, be affixed to a container which contains a pharmaceutical composition of the invention or be shipped together with a container which contains the pharmaceutical composition. Alternatively, the instructional material can be shipped separately from the container with the intention that the instructional material and the pharmaceutical composition be used cooperatively by the recipient.

In another embodiment, the invention includes a method of using an O-alkylated rapamycin derivative such as SDZ RAD or rapamycin to inhibit the establishment of a tumor in a mammal. This method involves administering to a mammal having a first tumor, an amount of the rapamycin derivative sufficient to inhibit establishment of a second tumor derived from the first tumor in the mammal. A mammal to be treated with an O-alkylated rapamycin derivative for this purpose can have substantially any type of first tumor such as a tumor of the brain, kidney, liver, breast, or ovary. Other representative anti-tumor activities that can be exhibited by an O-alkylated rapamycin derivative such as SDZ RAD include inhibition of tumorigenesis, inhibition of metastasis, inhibition of tumor cell growth, inhibition of tumor cell proliferation, and induction of tumor cell death.

In alternative embodiments, the present invention relates to methods of using an O-alkylated rapamycin derivative such as SDZ RAD to affect biological processes and elicit therapeutic responses related to the anti-proliferative, anti-tumor, and immunosuppressive activities exhibited by this compound. These methods include, for example, using the derivative to induce apoptosis, inhibit cell proliferation, or for anti-tumor, anti-PTLD, or immunosuppressive purposes. Thus, the derivative can be used to inhibit (i.e., ameliorate, prevent, or reduce the severity, frequency, rate, or extent) disorders associated with these processes. As effective anti-proliferative agents, O-alkylated rapamycin derivatives can be useful for alleviating substantially any disorder that is characterized by supra-normal or otherwise inappropriate cellular proliferation. Examples of disorders include auto-immune disorders, allergies, other hyper-immune disorders, atherosclerosis.

The invention includes a method of identifying an agent that is useful for alleviating or inhibiting a lymphoproliferative disorder in a mammal. This method comprise transforming a B lymphocyte by exposing it to EBV. Such exposure can be performed using standard reagents and techniques and employing any available strains of EBV which can transform lymphocytes. B lymphocytes useful for this method can, for example, be obtained from a human donor. Transformed B lymphocytes are injected into a mouse having a severe combined immunodeficiency, such as a SCID mouse. Transformed lymphocyte can be injected into the mouse intraperitoneally or subcutaneously. Preferably, the injection of the transformed B lymphocyte is subcutaneous. An agent potentially exhibiting anti-lymphoproliferative activity is also administered to the mouse. Tumor growth in the mouse is monitored for a selected period of time, such as for about 21 days. Inhibition of tumor growth or development is an indication that the agent exhibits anti-lymphoproliferative activity.

In one embodiment of the method, a potential anti-lymphoproliferative agent is administered to a SCID mouse prior to the injection of a transformed B lymphocyte. By way of example, an agent such as SDZ RAD can be administered to a SCID mouse at a dose of 5 milligrams per kilogram per day for at least about 10 days, and preferably, at least about 3 days prior to injecting the mouse with transformed B lymphocytes.

In another embodiment of the method, a potential anti-lymphoproliferative agent is administered to a SCID mouse after the injection of a transformed B lymphocyte and development of the resulting tumor in the mouse. In this embodiment the injection of transformed B lymphocytes is followed by at least about 21 days of monitoring the growth of the resulting tumor in the mouse, and administration of a potential anti-lymphoproliferative agent to the mouse beginning about after day 21. By way of example, an agent such as SDZ RAD can be administered to a SCID mouse at a dose of 5 milligrams per kilogram per day beginning at about day 21 post-injection.

Using the methods described herein, assessment of an agent as having anti-lymphoproliferative activity can be based on evidence of tumor regression (i.e., a decrease in tumor size relative to the initiation of treatment with the agent), tumor eradication, and the absence of a second tumor in the injected mouse. Likewise, an agent does not have substantial anti-lymphoproliferative activity if the injected mouse exhibits tumor growth (i.e., an increase in tumor size) or the development of a second tumor or both.

In other embodiments, the method described herein for identifying an anti-lymphoproliferative agent is also useful for identifying an agent capable of inhibiting establishment of a tumor (e.g., capable of inhibiting spread or metastasis of a lymphatic tumor) in a mammal. For example, an agent which inhibits establishment of a tumor in a mammal can be identified by exposing a B lymphocyte to EPV, such that a transformed B lymphocyte is generated, administering the agent to a mouse having a severe combined immunodeficiency, such as a SCID mouse, injecting the transformed B lymphocyte into the mouse, and monitoring tumor growth in the mouse for a selected period (e.g., at least about 21 days). An agent capable of inhibiting establishment of a tumor will cause one or more of tumor regression, tumor eradication, and absence of a second tumor in the injected mouse. An agent that is not capable of inhibiting establishment of a tumor will not have an observable affect on the injected mouse in terms of tumor growth and development of secondary tumors.

In reference to the methods described above, procedures for measuring tumor growth or regression, injecting B lymphocytes, and determining appropriate dosages at which to test potential anti-PTLD agents are within the ability of one skilled in the art of immunopharmacology. Upon reading the present disclosure and examining the particulars of Example 1 provided herein, it is a simple matter for the skilled artisan to use the methods of the present invention to identify compounds which exhibit anti-lymphoproliferative activity or which are capable of inhibiting establishment of a tumor.

The invention is now described with reference to the following Examples. These Examples are provided for the purpose of illustration only, and the invention is not limited to these Examples, but rather encompasses all variations which are evident as a result of the teaching provided herein.

EXAMPLE 1

SDZ RAD Inhibits Growth of Human EBV-Transformed B Lymphocytes In Vitro and In Vivo The experiments presented in this Example demonstrate that SDZ RAD is a potent anti-rejection, anti-lymphoproliferative agent, and represents a novel approach to inhibition and treatment of post-transplant lymphoproliferative disorders (PTLDs).

The materials and methods used in the experiments presented in this Example are now described.

Most cell lines used in this study were lymphoblastoid B-cell lines obtained by in vitro infection with EBV of peripheral blood mononuclear cells (PBMC). Cell lines A1 and A2D6 were obtained from normal, healthy individuals. Cell lines 15A and 20A were obtained from two different patients with a low grade B-cell lymphoma with monoclonal cold agglutinins (Silberstein et al., 1991, Blood 78:2372-2386). Both lines secreted cold agglutinins with the same specificity as the cold agglutinins found in the patient's serum (Silberstein et al., 1991, Blood 78:2372-2386). Furthermore, the 20A cell line exhibited cytogenetic abnormalities seen in low-grade lymphomas (48,XX, +3, +12, according to Silberstein et al., 1991, Blood 78:2372-2386). LCL B-cell line was obtained from a patient with a progressive cutaneous T-cell lymphoproliferative disorder (Zhang et al., 1996, Proc. Natl. Acad. Sci. USA 93:9148-9153). BC-1 is derived from a peritoneal effusion B-cell lymphoma (PEL) and, in addition to EBV, harbors HHSV8 virus (Cesarman et al., 1995, Blood 86:2708-2714). The other 3 cell lines used as controls in the in vitro growth inhibition assay were HTLV-I (+) T-cell lines ATL-2 (Maeda et al., 1985, Exp. Med. 162:2169-2174); C10MJ2 (Popovic et al., 1983, Science 219: 856-859); and HUT102B (Poiescz, 1980, Proc. Natl. Acad. Sci. USA 77:7415-7419; Bunn, et al, 1996, J. Cell. Biochem. Suppl 24:12-23) derived from patients with adult T-cell leukemia/lymphoma (ATLL). They were shown by us to be non-responsive to SDZ RAD and the related, immunosuppressive macrolide, rapamycin (Zhang et al., 1999, Leukemia Res. 23:373-384). All cell lines were maintained in humidified incubators at 37° C. in an atmosphere containing 5% $CO_2$ in standard medium: RPMI Medium 1640 (Gibco BRL, Grand Island, N.Y.) supplemented with 10% (v/v) heat inactivated fetal bovine serum (BioWhittaker, Walkersville, Md.), 1% penicillin/streptomycin/fungizone mixture (Gibco BRL), and 2 millimolar L-glutamine (Gibco BRL).

An assay to assess inhibition of in vitro cell growth by SDZ RAD was performed as described (Zhang et al., 1999, Leukemia Res. 23:373-384; Zhang et al., 1996, Proc. Natl. Acad. Sci. USA 93:9148-9153). Briefly, cell lines were cultured for 32 hours in triplicate at $2\times10^4$ cells per well in the presence of various concentrations of SDZ RAD (Novartis Pharma, Base1). After pulsing the cells with 0.5 microcurie $^3$H-thymidine (New England Nuclear, Boston, Mass.) and culturing the cells for the next 18 hours, isotope incorporation into the cells was measured. The results of proliferation assays were expressed as the mean radioactivity of triplicate cultures. Standard deviation within the triplicates was <15%.

Detection of Cell Cycle Inhibition and Apoptosis.

The cell lines to be examined were cultured with several concentrations of SDZ RAD (0 to 10 nanomolar) for 24-48 hours. The cells were washed with DPBS and stain solution (pH 7.2) containing 3% PEG 6000, 50 micrograms per milliliter DNA fluorochrome propidium iodide (PI; Calbiochem, San Diego, Calif.), annexin V-FITC as described (Douglas et al., 1998, Cytometry 32:57-65) 0.1% (v/v) TRITON™ X (Sigma, St. Louis, Mo.), 4 millimolar citrate buffer pH 7.8, and 360 units per milliliter RNase A (Worthington Biochemicals, Freehold, N.J.) for 30 minutes at 37 C. Next, salt solution pH 7.2 (3% w/v PEG 6000, PI 50 micrograms per milliliter, 0.1% v/v TRITON™ X, and 0.4 molar NaCl) was added, and the cells were incubated at 4° C. in the dark for 1 hour before flow cytometry analysis was performed, as described (Douglas et al., 1998, Cytometry 32:57-65; Kawamata et al., 1998, Blood 91:561-569; Pepper et al., 1998, Leuk. Res. 22:439-444).

Five- to seven-week-old immunodeficient SCID mice (C.B-17 and ICR) were purchased from Taconic (Germantown, N.J.) and housed at the University of Pennsylvania Animal Facility under pathogen-free conditions in a laminar air flow unit and supplied with sterile food and water. In the toxicity studies, 5-7 week old inbred BALB/c mice (Taconic) were used in addition to the SCID mice.

Establishment and passaging of the xenotransplanted tumors was performed as described (Douglas et al., 1998, Cytometry 32:57-65; Kawamata et al., 1998, Blood 91:561-569; Pepper et al., 1998, Leuk. Res. 22:439-444). To deplete macrophages and NK cells and to enhance tumor engraftment, SCID mice were injected intraperitoneally with 30-45 milligrams per kilogram of etoposide (Bedford Laboratories, Bedford, Ohio) 4 days prior to implantation of the human EBV$^+$ B-cell lines (Visonneau et al., 1998, Am. J. Path. 152: 1299-1311). Ten million cells of each line employed (see results) were inoculated into mice either intraperitoneally or subcutaneously in 200 microliters of Dulbecco's Phosphate Buffered Saline (DPBS; BioWhittaker, Walkersville, Md.). Ascites or palpable subcutaneous tumors developed 3-5 weeks after cell injection.

Tumor treatment and growth inhibition experiments were performed using fragments of the established subcutaneous tumors (Pasqualucci et al., 1995, Blood 85:2139-2146, Visonneau et al., 1998, Am. J. Path. 152:1299-1311). For this purpose, mice were anesthetized with KETALAR™ (ketamine, Parke-Davis, Morris Plains, N.J.) by intraperitoneal injection of 100 milligrams per kilogram. Next, the primary tumor was aseptically removed and freed from necrotic, fatty and connective tissue and divided into small pieces of roughly equal size and 3-4 pieces per mouse were injected subcutaneously. Treatment of established tumors with SDZ RAD was started when tumors reached 5 millimeters diameter. In growth inhibition experiments, the treatment was initiated 3 days prior to the tumor implantation. Tumor volume in all experiments was determined from the equation: volume=$0.4ab^2$, where a and b designate respectively long and short diameter of the tumor. The transplanted mice were monitored for tumor growth for a period of up to 2 months. Five milligrams per kilogram of SDZ RAD was administered once a day by gavage as described (Schuurman et al., 1997, Transplantation 64:32-5; Schuler et al. 1997, Transplantation 64:36-42).

Mice were sacrificed by exposure to FORANE™ (isoflurane, Ohmeda, Liberty Place, N.J.) on day 29 in the drug toxicity study, on day 40-55 in the tumor growth inhibition study or when tumors achieved approximately 2 centimeter diameter, or when ulceration of the skin, signs of severe respiratory distress, weakness, or lethargy appeared. Complete autopsy was performed on all mice at the end of the study regardless of their appearance. Tumor and internal organs (spleen, liver, lung, heart, kidney, small and large intestines, femoral bone for bone marrow) were fixed in 10% (v/v) formalin, embedded in paraffin, cut into 0.4 micron sections, transferred to glass slides, and stained with hematoxylin and eosin. Representative tumor fragments were stained immunohistochemically by standard streptavidin-biotin complex technique using commercially available reagents (Research Genetics, Huntsville, Ala.), antibodies: anti-CD20 (L-26) and LMP-1 (both from DAKO, Carpinteria, Calif.) and Ki67 (mibl; Immunotech, Westbrook, Me.). EBV-encoded RNA (EBER-1), and detected using commercially available reagents.

The results of the experiments presented in this Example are now described.

SDZ RAD Inhibits Growth of EBV$^+$ B Cells In Vitro

Figure 1:
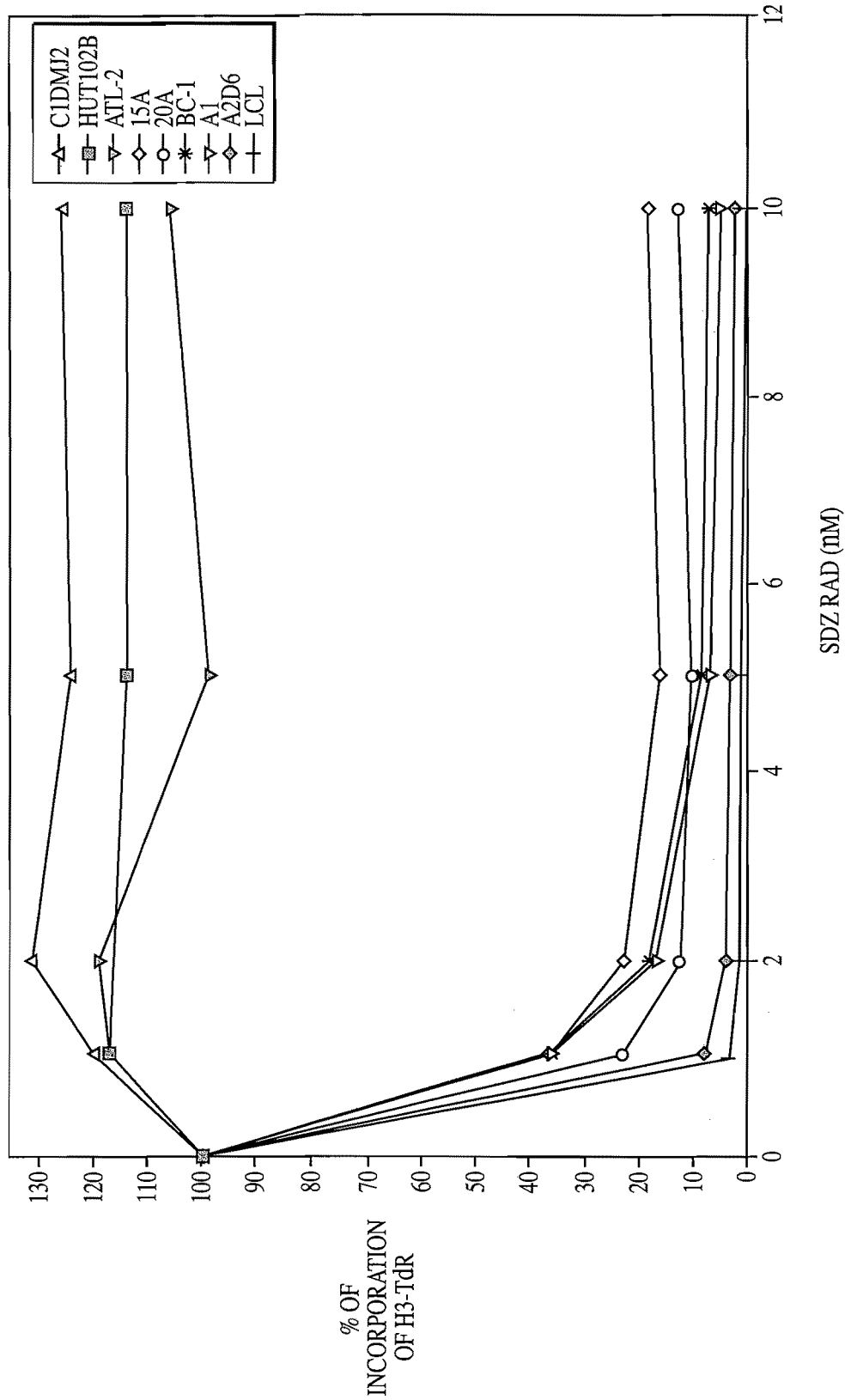
FIG. 1 is a graph which illustrates SDZ RAD-mediated inhibition of in vitro proliferation of PTLD-like EBV+ B cells. BC-1 is an EBV+/HSV8+ B-cell line derived from primary effusion lymphoma (PEL). The other cell lines are in vitro EBV-transformed B-cell lines derived from one of a patient with low-grade B-cell lymphoma (15A or 20A), a patient with T-cell lymphoma (LCL) or a healthy individual (A1 or A2D6). The HTLV-I+ malignant T-cell lines, HUT-102, C10MJ, and ATL-2, were included as control cell lines.

In order to determine whether SDZ RAD can inhibit proliferation of cells mimicking PTLDs, 6 different EBV$^+$ B cell lines were cultured in vitro in the presence of the drug at various concentrations. Three HTLV-I$^+$ T-cell lines resistant to SDZ RAD (Zhang et al., 1999, Leukemia Res., 23:373-384) were used as controls. As shown in FIG. 1, all PTLD-like EBV$^+$ B cell lines were very sensitive to SDZ RAD. A dose of SDZ RAD as small as 1 nanomolar produced 60-95% inhibition of growth in all cell lines. This result was comparable to the inhibition of stimulated normal T lymphocytes (Schuurman et al., 1997, Transplantation 64:32-5; Bohler et al., 1998, Transplant. Proc. 30:2195-2197). Some subtle differences in the degree of response were noted among the EBV+ B-cell lines. The lines derived from patients with B-cell lymphomas (15A, 20A and BC-1; see Materials and Methods), and thus resembling more the advanced forms of PTLD, tended to show a lower degree of inhibition (80-90%). Cell lines obtained from normal B cells (i.e., mimicking the less advanced types of PTLD) were inhibited more profoundly (90-100%). The cell lines were pulsed for 18 hours with tritiated thymidine after 32 hours culture with 0-10 nanomolar SDZ RAD.

SDZ RAD Blocks Cell Cycle Progression in EBV+ B Cells

Figure 2:
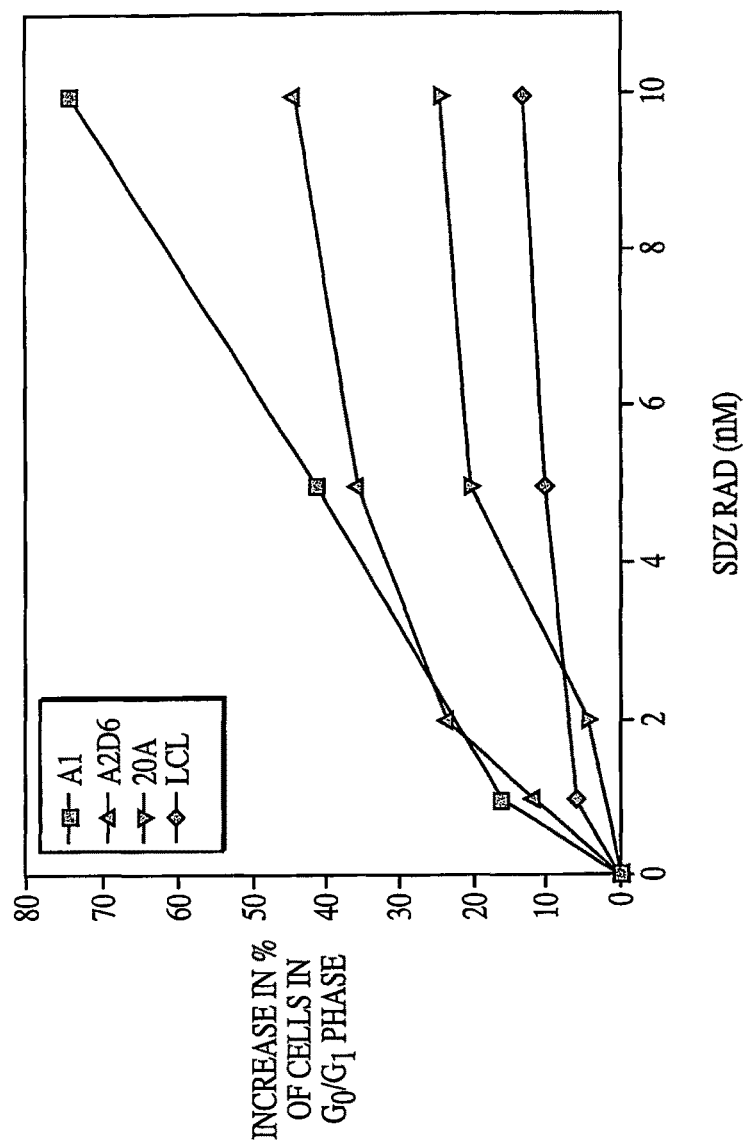
FIG. 2 is a graph which illustrates SDZ RAD-mediated inhibition of cell cycle progression in PTLD-like B cells. Four EBV+ B-cell lines were cultured for 48 hours in the presence of 0-10 nanomolar SDZ RAD, labeled with propidium iodine, and analyzed by flow cytometry.

Rapamycin and, presumably, O-alkylated rapamycin derivatives such as SDZ RAD, block cell cycle progression at the early stage in normal T cells (Terada et al., 1993, J. Cell Physiol. 154:7-15; Flanagan et al., 1993, Ann. N.Y. Acad. Sci. 696:31-37). Our cell growth inhibition data which measured incorporation of thymidine (FIG. 1), suggested that SDZ RAD inhibits cell cycle progression in PTLD-like B cells. As shown in FIG. 2, SDZ RAD markedly inhibited cell cycle progression at the early, $G_0/G_1$ phase in all 4 PTLD-like B cell lines investigated: 20A, A1, A2D6, and LCL. The effect was drug dose and cell-line type dependent. Whereas the low SDZ RAD doses (1-2 nanomolar) increased the percentage of cells in $G_0/G_1$ by 5-25, the highest dose tested (10 nanomolar) resulted in the 10-70% increase. Percentages of cells in the later phases of the cell cycle ($G_2$-M and S) were diminished proportionally. A1 and, to a lesser degree, A2D6 cell line were particularly sensitive to SDZ RAD. Four EBV+ B-cell lines were cultured for 48 hours with 0-10 nanomolar SDZ RAD, labeled with propidium iodine, and analyzed by flow cytometry.

SDZ RAD Increases Apoptosis in EBV+ B Cells

Figure 3:
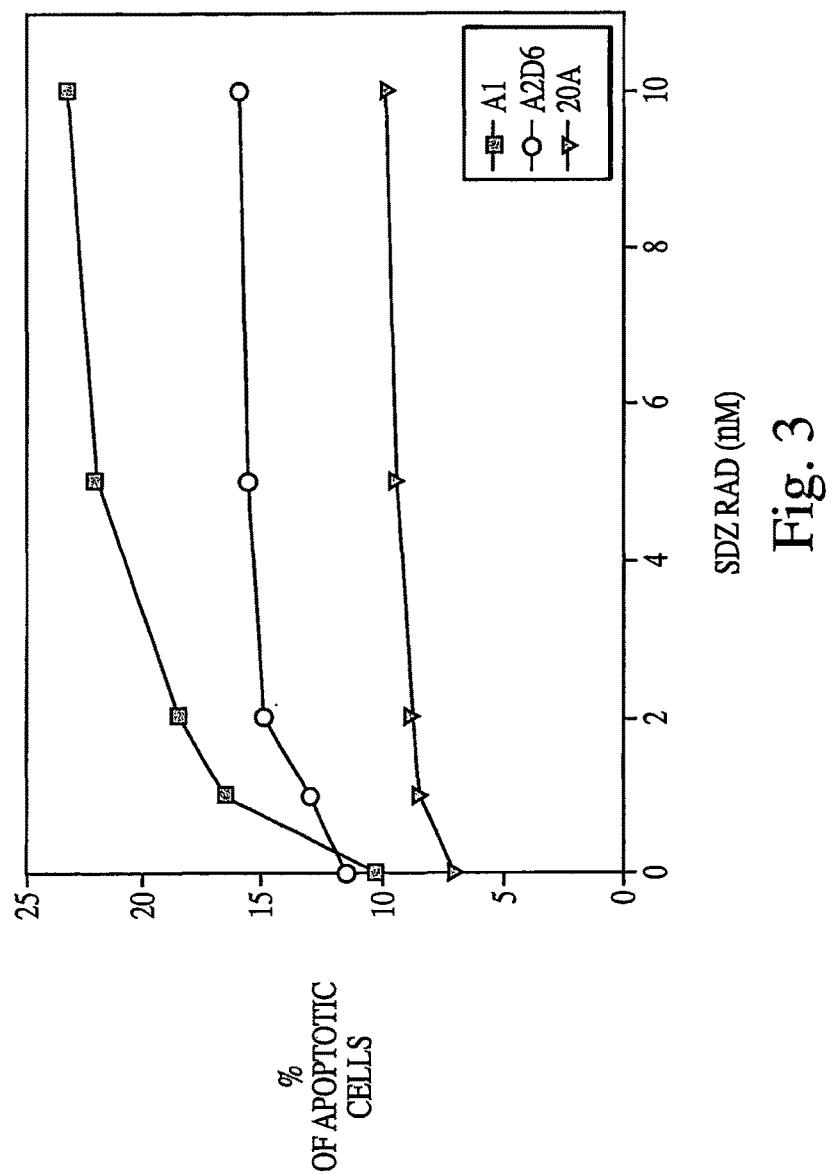
FIG. 3 is a graph which illustrates SDZ RAD-mediated increase in apoptotic rate of PTLD-like B cells. Three EBV+ B-cell lines were cultured for 24 hours in the presence of 0-10 nanomolar SDZ RAD, labeled with propidium iodine and anti-Annexin V antibody, and analyzed by flow cytometry.

Previous studies have shown that immunosuppressive macrolides as represented by rapamycin can induce or enhance apoptosis stimulated by other agents (Gottschalk et al., 1994, Proc. Natl. Acad. Sci. USA 91:7350-7354; Muthukkumar et al., 1995, Transplantation 60:264-270; Shi et al., 1995, Cancer Res. 55:1982-1988; Hosoi et al., 1999, Cancer Res. 59:886-894). In order to determine if SDZ RAD affects the apoptotic rate in PTLD-like cells, we tested apoptosis-induced surface expression of Annexin V by flow cytometry in the 20A, A1, A2D6 cell lines (FIG. 3). Even the lowest SDZ RAD dose (1 nanomolar) markedly increased the percentage of apoptotic cells in all cell lines, with some differences resembling the cell growth and cell cycle inhibition data. In the most sensitive A1 line, SDZ RAD resulted in approximately 60% increase in the number of apoptotic cells from 10 to 16%. In A2D6 line, it led to 11% increase, and in the 20A line to 12% increase. At the highest dose (10 nanomolar), SDZ RAD led to approximately 240% increase in A1 line and 45% increase in both A2D6 and 20A lines.

Toxicity Study

Previous studies have shown that a minimal effective dose of SDZ RAD in rats was 5 milligrams per kilogram body weight per day and >5 milligrams per kilogram body weight per day in the in kidney and heart transplant model, respectively, when SDZ RAD was used as a single immunosuppressive agent (Schuurman et al., 1997, Transplantation 64:32-5; Schuler et al. 1997, Transplantation 64: 36-42). In order to determine if prolonged exposure to SDZ RAD is non-toxic for mice, both immunocompetent and immunodeficient, a cohort of normal BALB/c mice were treated with the above dose of SDZ RAD for 28 days. Ten treated and 5 control, untreated mice were used in this study. Later SCID mice which were transplanted with human PTLD-like lymphomas and treated with SDZ RAD for up to 55 days were evaluated. Seven treated and 5 control untreated SCID mice were evaluated in this experiment. After receiving the final dose of the drug, all mice were sacrificed and the following organs were harvested for histopathologic evaluation to investigate for possible toxic effects: liver, spleen, kidney, small intestine, large intestine, heart, lung, and femoral bone for bone marrow.

None of the treated mice showed any visible signs of drug toxicity. Growth and weight gain were the same for the SDZ RAD-treated and the control group. Microscopic evaluation of the organs of all treated and untreated mice revealed no pathologic changes which could be attributed to the drug. We conclude, therefore, that prolonged exposure to SDZ RAD at the dose of 5 milligrams per kilogram body weight per day has no adverse effect in the treated mice, regardless of their immune status.

Establishment of the xenotransplant model of human PTLD-like lymphoma in SCID mice.

In these experiments, mice were injected with EBV+ B-cell lines via two different routes: intraperitoneal and subcutaneous. In the intraperitoneal tumor model, SCID mice (5 per group) were inoculated intraperitoneally with about $10^7$ cells per line from four cell lines: 15A, 20A, A2D6 and BC-1. After 21-35 days, all mice developed fatal disease with ascites and symptoms of weakness or lethargy. Autopsy revealed extensive tumor infiltrates involving peritoneal wall, liver, spleen, and kidneys. Microscopic examination of the tumors showed a large cell lymphoma with an infiltrative growth pattern, high mitotic rate, focal and single-cell necrosis and some degree of plasmacytoid differentiation. Foci of the lymphoma were also present in distant organs such as lungs and bone marrow indicating hematogeneous spread.

In the subcutaneous model, mice (also 5 per group) were injected with about $10^7$ cells from the 15A, 20A and A1 lines. After 21-32 days, all mice developed tumors in the site of implantation. Autopsy revealed subcutaneous tumors invading adjacent skeletal muscle and skin. There was no gross evidence of distant spread of the tumor. Microscopic examination revealed the same type of high-grade lymphoma as in the intraperitoneal model. Distant internal organs, mainly liver and lungs occasionally displayed small tumor foci. This occurred only when the subcutaneous lymphoma reached a relatively large size of at least 1.5 cm in diameter. Immunohistochemical staining confirmed that the tumors were derived from the implanted human EBV+ B lymphocytes. The images of the 20A line shown in FIG. 4A-D are representative for all three cell lines.

Virtually all lymphoma cells were positive for human B-cell marker CD20. Most (50-80%) were positive for cell-cycle related Ki-67 antigen consistent with their high proliferative rate. Staining for EBV-related antigen EBER1 was universally positive (100% of cells). Twenty to 50% of cells expressed EBV-associated latent membrane protein 1 (LMP-1). These results confirm that tumors represent human EBV+ B-cell lymphoma corresponding to the monomorphic type of PTLD.

The subcutaneous lymphoma model had some advantages over the peritoneal model. First, even small lymphomas could be easily identified. Second, the lymphomas of up to 1.5 centimeters diameter remained localized which permitted determination of total tumor volume with great accuracy (Wasik et al., 1994, Am. J. Path. 144:1089-1097). Finally, the subcutaneous tumor could be transferred simultaneously into several mice by implanting tumor tissue fragments rather than single-cell suspension (Wasik et al., 1994, Am. J. Path. 144: 1089-1097; Pasqualucci et al., 1995, Blood 85:2139-2146; Visonneau et al., 1998, Am. J. Path. 152:1299-1311). Such implantation results in a fast establishment of tumors with very similar growth characteristics in virtually all recipient mice (Wasik et al., 1994, Am. J. Path. 144:1089-1097; Pasqualucci et al., 1995, Blood 85:2139-2146; Visonneau et al., 1998, Am. J. Path. 152:1299-1311). For these reasons, we selected the subcutaneous model for further studies.

Treatment of Established EBV$^+$ B-Cell Tumors.

In order to determine the in vivo effect of SDZ RAD on PTLD-like cells, 15A, 20A, and A1 cell line tumors were implanted into 7-15 SCID mice per cell line. Treatment was initiated once the tumors reached 5 millimeters diameter, which corresponds to a volume of 50 cubic millimeters. SDZ RAD was administered by daily gavage at 5 milligrams per kilogram, which represents a non-toxic and effective immunosuppressive dose (Schuurman et al., 1997, Transplantation 64:32-5; Schuler et al. 1997, Transplantation 64:36-42).

Figure 5A:
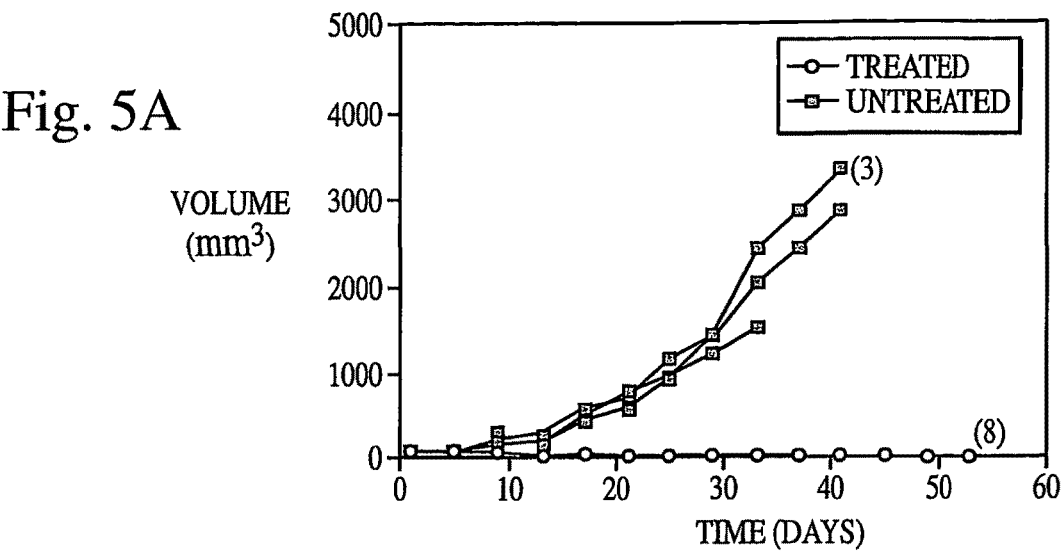
FIGS. 5A-5C, is a trio of graphs which illustrates SDZ RAD-mediated inhibition of in vivo growth of PTLD-like B-cells; treatment of established tumors. Fragments of tumors derived from EBV+ B-cell lines 15A (FIG. 5C), 20A (FIG. 5B), and A1 (FIG. 5A) were implanted into recipient SCID mice. The number of mice per group is indicated in parentheses. Treatment with 5 milligrams per kilogram body weight per day of the drug was started when the tumors reached 0.4-0.5 cm in diameter.
Figure 5B:
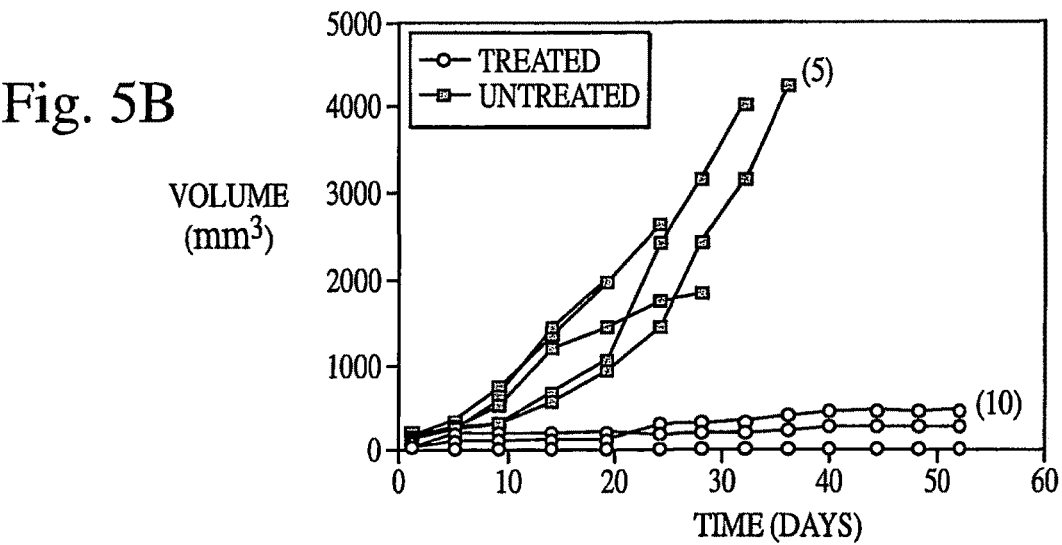
Figure 5C:
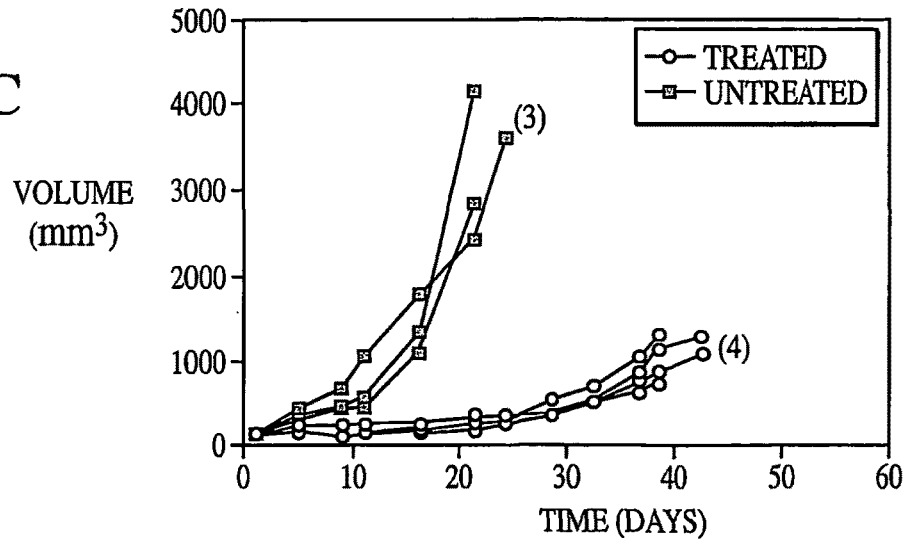

As shown in FIG. 5, SDZ RAD had a profound inhibitory effect on growth of the xenotransplanted PTLD-like tumors with visible differences in the degree of response among the three tumors. In mice implanted with 15A tumors, there was a marked drug-induced delay of the tumor growth but no absolute tumor growth inhibition or regression. On day 21, the median tumor volume was approximately 240 cubic millimeters in the treated mice and 2720 cubic millimeters in the control, untreated mice. As late as on day 38, 15A tumors in the treated mice reached only around 1000 cubic millimeters. The effect of SDZ RAD on the 20A tumors was even more striking. Whereas on day 19, the control 20A tumors displayed the median volume of 1440 cubic millimeters, the average treated tumor measured only 50 cubic millimeters, which was equal to the initial tumor size. Furthermore, a significant regression in the tumor volume was seen in 6 out of 10 treated mice. Accordingly, the median tumor volume on day 53 was only <5 cubic millimeters for this subset.

SDZ RAD proved to be the most effective against the A1 cell line. On day 21 median volume of the treated tumors was 50 cubic millimeters, with none of the tumors (0/8) showing any evidence of growth. Mean volume of the untreated tumors on that day was approximately 1800 cubic millimeters. Further treatment resulted in a steady regression in all 8 mice. On day 53, the mean tumor volume decreased to <5 cubic millimeters, and no lymphoma could be detected in 4 mice, indicating total tumor eradication. The other 4 mice had microscopically-confirmed residual lymphoma. Noteworthy, the differences in the in vivo effectiveness of SDZ RAD against the 15A, 20A, and A1 tumors paralleled the differences seen in the proliferation (FIG. 1) and the other in vitro assays (FIGS. 2 and 3). This observation suggests that the cell analysis in vitro is predictive of the response to SDZ RAD in vivo.

Inhibition of Tumor Establishment

Figure 6A:
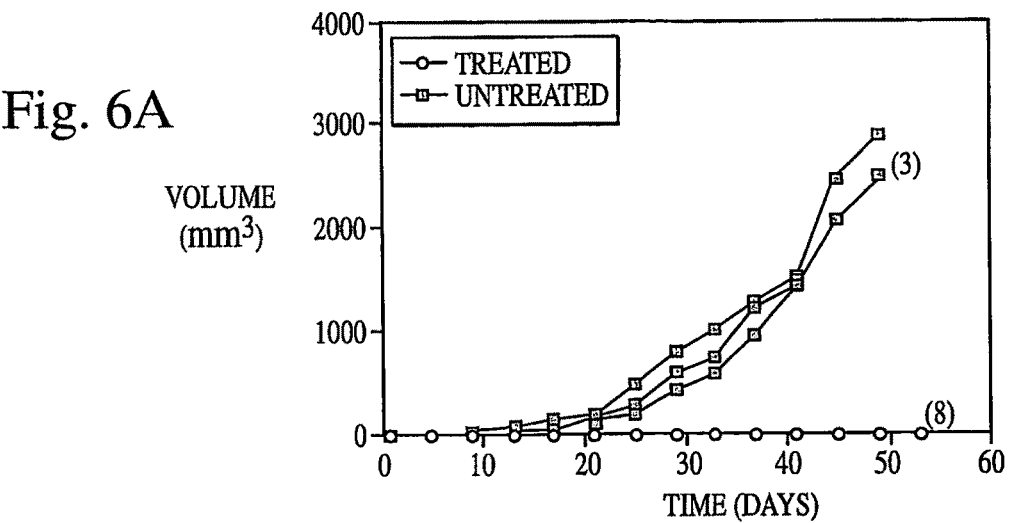
FIGS. 6A-6C, is a trio of graphs which illustrates SDZ RAD-mediated inhibition of in vivo growth of a malignant PTLD-like B-cells (i.e., inhibition of tumor growth). Fragments of tumors derived from EBV+ B-cell lines 15A (FIG. 6C), 20A (FIG. 6B), and A1 (FIG. 6A) were implanted into recipient SCID mice. The number of mice per group is indicated in parentheses. The treatment with 5 milligrams per kilogram body weight per day of the drug was started 3 days prior to the tumor implantation.
Figure 6B:
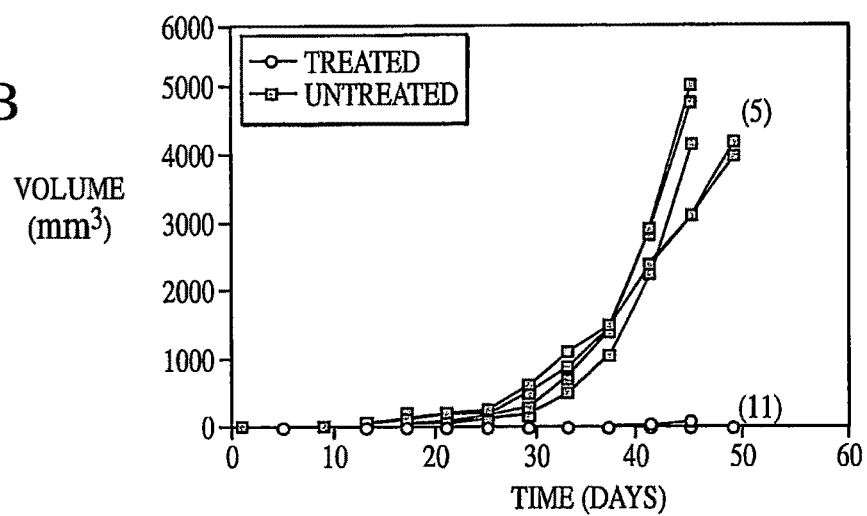
Figure 6C:
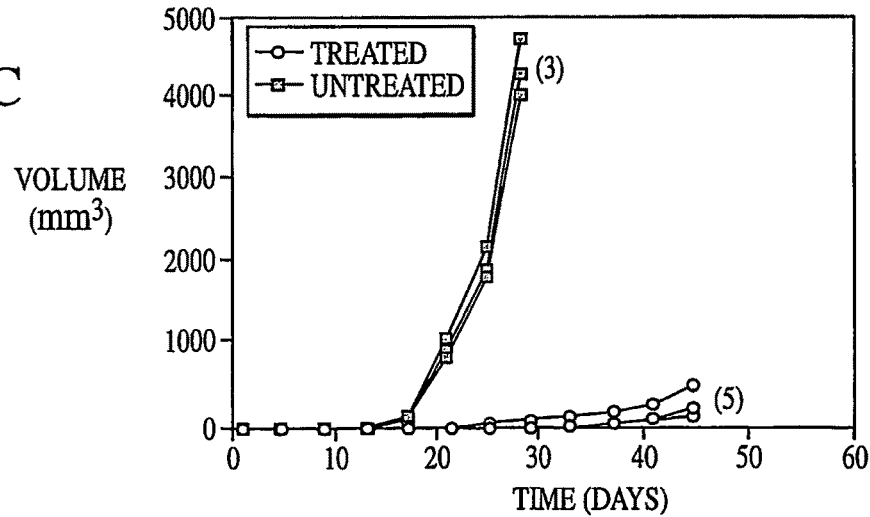

Because SDZ RAD, when used as an immunosuppressive agent, is administered chronically to transplant patients, its main therapeutic impact on PTLDs may be to inhibit their development rather than to alleviate the clinically symptomatic cases. To test if SDZ RAD can inhibit establishment of PTLD-like lymphomas, daily treatment with 5 milligrams per kilogram body weight of the drug was initiated 3 days prior to the tumor implantation. As shown in FIG. 6, SDZ RAD proved to be extremely effective in this model. In 15A tumors, which are the least sensitive to SDZ RAD (FIG. 5), treatment with SDZ RAD profoundly delayed the tumor growth, but was unable to inhibit the tumor establishment. On day 25, the treated tumors measured in average 38 cubic millimeters, the untreated approximately 1940 cubic millimeters. On day 45, the median volume of the treated tumor was 480 cubic millimeters. In 20A tumors, 6 out of 11 tumors were not detectable on day 25; the median volume of the remaining 5 was 20 cubic millimeters. The average untreated tumor measured 210 cubic millimeters on that day. On day 45, none of the treated tumors exceeded 150 cubic millimeters, the average untreated tumor measured approximately 4200 cubic millimeters. Five treated mice showed no signs of tumor; microscopic evaluation of the implantation site revealed no malignant cells. Finally, in A1 mice no tumor could be detected as late as on day 29 in any of the 8 treated mice; the average tumor in the untreated mice measured 580 cubic millimeters. On day 53 only 3 mice showed small (<5 cubic millimeters), histologically confirmed lymphomas. The remaining 5 mice showed no evidence of tumor.

Whereas the standard immunosuppressive agents foster development of PTLDs, the impact of SDZ RAD and other macrolides on these disorders remains undetermined. It was observed that SDZ RAD profoundly suppressed in vitro lymphocyte proliferation, blocked cell cycle progression, and increased apoptotic rate in PTLD-like EBV B cells. In the in vivo SCID mouse xenotransplant model, SDZ RAD markedly delayed growth or induced regression of established EBV$^+$ B-cell tumors. The drug completely eradicated or inhibited tumor establishment in a subset of the treated mice. These findings indicate that macrolides such as SDZ RAD may be effective in inhibition and treatment of PTLDs.

SDZ RAD profoundly suppressed in vitro proliferation, arrested cell cycle progression at the early, $G_0/G_1$ stage, and increased apoptotic rate in PTLD-like EBV$^+$ B cells. In the SCID mice xenotransplanted with three different PTLD-like B-cell tumors, SDZ RAD markedly inhibited growth of these tumors, particularly if administered prior to tumor implantation. In the A1 tumors, total eradication of already established tumors was achieved in 4 out of 8 (4/8) mice. In two of the three lines tested (20A and A1), SDZ RAD completely inhibited establishment of tumors in approximately 50% of mice (5/11 and 5/8, respectively). The anti-EBV$^+$ B-cell tumor property of SDZ RAD contrasts with the standard immunosuppressive agents cyclosporin and tacrolimus, which have been suggested recently to enhance outgrowth of EBV$^+$ B cells, not only indirectly by suppressing an immune response against such cells, but also directly by protecting them from the effects of pro-apoptotic signals (Beatty et al., 1998, Transplantation 65:1248-1255.)

The results of these experiments are particularly encouraging because 15A and 20A lines were derived from lymphoma cells (Silberstein et al., 1991, Blood 78:2372-2386) and, as such, appear to correspond to the advanced, clinically aggressive form of PTLD. It is plausible, therefore, that other, less malignant forms of PTLD which comprise majority of cases, should be even more sensitive to SDZ RAD. The fact that the A1 cell line obtained from a normal individual was more sensitive than 15A and 20A to SDZ RAD, supports this assumption.

The data presented in this Example also suggest that monotherapy with SDZ RAD may not be sufficient to eradicate some established, overtly malignant PTLD tumors, and that combination therapy using both SDZ RAD (or another O-alkylated rapamycin derivative or rapamycin) and one or more conventional chemotherapeutic drugs can considered in the clinical setting (Shi et al., 1995, Res. 55:1982-1988; Miki et al., 1998, Transplant. Proc. 30:1091-1092).

Although inhibition of cell growth, as measured by thymidine incorporation (FIG. 1) and cell cycle progression (FIG.

2), appears to be the main mode of SDZ RAD action on EBV+ B cells, the results described herein that SDZ RAD also increases apoptotic rate in such cells (FIG. 3), suggests that programmed cell death may also be an important component of anti-tumor activity of the drug. This pro-apoptotic effect can be particularly important in treatment of established PTLD tumors, where inhibition of tumor growth alone might not be sufficient to achieve complete tumor regression. The observation herein that only prolonged exposure to SDZ RAD led to marked regression or elimination of many tumors (FIG. 5), suggests that a similar extended treatment may be desirable to eradicate established PTLDs.

Although PTLD-like B-cell lines sensitive to SDZ RAD were all EBV+, the potential role, if any, of the virus in mediating this sensitivity is not fully understood. EBV encodes or induces in the target cells several proteins capable of activating cytokine signaling pathways (Rochford, et al., 1997, Viral Immunol 10:183-195). The membrane-anchored viral protein designated LMP-1 is the best characterized, and uses the TRAF signaling pathway of the TNF receptor family (Mosialos et al., 1995, Cell 80:389-399; Devergne et al., 1998, J. Virol. 72:7900-7908; Liebowitz et al., 1998, New Eng. J. Med. 338:1413-1421). It is interesting in this context, that signaling via CD40 which belongs to the family and shares several features with LMP-1 including signaling via TRAF3 protein (Eliopoulos et al., 1996, Oncogene 13:2243-2254; Pullen et al., 1998, Biochemistry 37:11836-11845) has been shown recently to be inhibited by rapamycin (Sakata et al., 1999, Immunology Letters 68:301-309). Immunohistochemical analysis indicates that LMP-1 is expressed only by a subset of EBV+ B cells, which suggests that LMP-1 may not be critical for growth of the PTLD-like cells and their sensitivity to SDZ RAD. EBV encodes also two other, related membrane proteins, designated LMP-2A and LMP-2B. These proteins do not appear to be essential for in vivo growth of EBV+ B cells (Rochford et al., 1997, Arch Virol 142:707-720). Alternatively, SDZ RAD might inhibit signaling mediated by cytokines induced by EBV in the target cells such as TNF-alpha and TNF-beta (Rochford, et al., 1997, Viral Immunol 10:183-195).

SDZ RAD exhibits potent inhibitory activity on the PTLD-like, EBV+ lymphoblastoid B-cell lines, both in vitro and in vivo. SDZ RAD profoundly inhibits in vitro proliferation of such cells and arrested their cell cycle progression at the early, $G_0/G_1$ stage. In addition, the drug increases apoptotic rate of EBV+ B cells. In vivo, it markedly delays or completely inhibits growth of EBV+ B cells xenotransplanted into SCID mice, particularly when administered prior to cell implantation. SDZ RAD is able to eradicate an established tumor in some instances. This effect appears to be cell line-specific and proportional to the drug effect seen in vitro.

In summary, the data presented in this Example demonstrate that SDZ RAD has a potent inhibitory effect on EBV+ B lymphocytes in vitro and in vivo. Therefore, it can be effective in treatment and inhibition of PTLDs in transplant patients or in treatment and inhibition of other lymphoproliferative disorders.

New treatment modalities are needed to inhibit development and improve cure rate of PTLDs. An ideal anti-PTLD drug would play a double role of inhibiting graft rejection and, at the same time, inhibiting development and growth of PTLD. Should PTLD develop despite the treatment, an increase, rather than a decrease in the drug dose as is currently done with the standard immunosuppressive drugs, might be effective. This approach of increasing the drug dose would have an additional advantage of not jeopardizing survival of the graft. This Example presents in vitro and in vivo data which indicate that SDZ RAD, a macrolide immunosuppressive agent, has the dual roles of an anti-rejection agent and an anti-lymphoproliferative agent.

The disclosure of every patent, patent application, and publication cited herein is hereby incorporated herein by reference in its entirety.

While this invention has been disclosed with reference to specific embodiments, it is apparent that other embodiments and variations of this invention can be devised by others skilled in the art without departing from the true spirit and scope of the invention. The appended claims include all such embodiments and equivalent variations.

What is claimed is:

1. A method of inhibiting metastasis of a lymphatic tumor in a human patient afflicted with a lymphatic cancer, the method comprising administering to the patient, in an amount sufficient to inhibit lymphocyte proliferation, a rapamycin derivative having the chemical structure

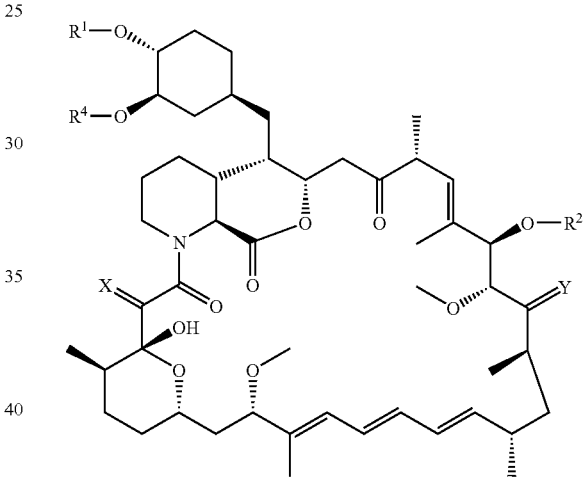

wherein
X is (H, H) or O;
Y is (H, OH) or O;
each of $R^1$ and $R^2$ independently ndependently selected from the group consisting of —H, alkyl, thioalkyl, arylalkyl, hydroxyalkyl, dihydroxyalkyl, hydroxyalkylarylalkyl, dihydroxyalkylarylalkyl, alkoxyalkyl, acyloxyalkyl, aminoalkyl, alkylaminoalkyl, alkoxycarbonylaminoalkyl, acylaminoalkyl, arylsulfonamidoalkyl, allyl, dihydroxyalkylallyl, dioxolanylallyl, carbalkoxyalkyl, and $(R^3)_3$ Si;
each $R^3$ is independently selected from the group consisting of —H, methyl, ethyl, isopropyl, tert-butyl, and phenyl; and
either $R^4$ is methyl or $R^4$ and $R^1$ together form a $C_{2-5}$ alkylene moiety.

2. The method of claim 1, wherein the rapamycin derivative is 40-O-(2-hydroxy)ethyl-rapamycin.

* * * * *